(12) United States Patent
Tuck et al.

(10) Patent No.: US 11,786,413 B2
(45) Date of Patent: Oct. 17, 2023

(54) MEDICAL DRAPES AND METHODS FOR REDUCING TRAUMA ON REMOVAL

(71) Applicant: KCI Licensing, Inc., San Antonio, TX (US)

(72) Inventors: Robert Tuck, Hampshire (GB); David Richard Mercer, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 822 days.

(21) Appl. No.: 16/732,915

(22) Filed: Jan. 2, 2020

(65) Prior Publication Data

US 2020/0138633 A1     May 7, 2020

Related U.S. Application Data

(62) Division of application No. 15/341,857, filed on Nov. 2, 2016, now Pat. No. 10,568,773.

(Continued)

(51) Int. Cl.
*A61F 13/02*     (2006.01)
*A61L 31/02*     (2006.01)
(Continued)

(52) U.S. Cl.
CPC ...... *A61F 13/025* (2013.01); *A61F 13/00068* (2013.01); *A61F 13/0216* (2013.01); *A61F 13/0233* (2013.01); *A61F 13/0253* (2013.01); *A61F 13/0256* (2013.01); *A61F 13/0266* (2013.01); *A61L 31/028* (2013.01); *A61L 31/048* (2013.01); *A61M 1/90* (2021.05)

(58) Field of Classification Search
CPC ............... A61F 13/025; A61F 13/0253; A61F 13/0256; A61F 13/02–0266; A61M 1/0088

See application file for complete search history.

(56) References Cited

U.S. PATENT DOCUMENTS 1,355,846 A    10/1920   Rannells
2,547,758 A    4/1951   Keeling
(Continued)

FOREIGN PATENT DOCUMENTS

AU         550575 B2    3/1986
AU         745271 B2    3/2002
(Continued)

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Susan S Su

(57) ABSTRACT

In some illustrative examples, a medical drape suitable for treating a tissue site may include an adherent surface including first adherent force profile oriented along a first axis and a second adherent force profile oriented along a second axis. The first adherent force profile may have an average force less than an average force of the second adherent force profile. Other apparatuses, systems, and methods are also provided.

18 Claims, 8 Drawing Sheets

Related U.S. Application Data

(60) Provisional application No. 62/257,082, filed on Nov. 18, 2015.

(51) Int. Cl.
  *A61L 31/04* (2006.01)
  *A61F 13/00* (2006.01)
  *A61M 1/00* (2006.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,804,021 A * | 9/1998 | Abuto | B32B 27/40 428/152 |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2008/0154169 A1 * | 6/2008 | Kase | A61F 13/025 602/55 |
| 2009/0062763 A1 * | 3/2009 | Hancock-Cooke | A61F 13/49466 604/385.24 |
| 2010/0130952 A1 * | 5/2010 | Murai | A61F 13/495 604/385.24 |
| 2013/0152945 A1 * | 6/2013 | Locke | A61F 13/00068 128/849 |
| 2014/0012213 A1 * | 1/2014 | Locke | A61F 13/0216 156/252 |
| 2014/0155791 A1 * | 6/2014 | Robinson | A61F 13/0269 601/7 |
| 2014/0163491 A1 | 6/2014 | Schuessler et al. | |

(56) References Cited

U.S. PATENT DOCUMENTS

| | | | | |
|---|---|---|---|---|
| 2014/0276490 A1* | 9/2014 | Locke | ............... | A61F 13/0216 604/319 |
| 2015/0080788 A1 | 3/2015 | Blott et al. | | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | WO-2007109593 A2 * | 9/2007 ........... A61F 13/025 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds" Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract,

(56) References Cited

OTHER PUBLICATIONS editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
VAC.® Therapy Clinical Guidelines: A Reference Source for Clinicians; Jul. 2007.

\* cited by examiner

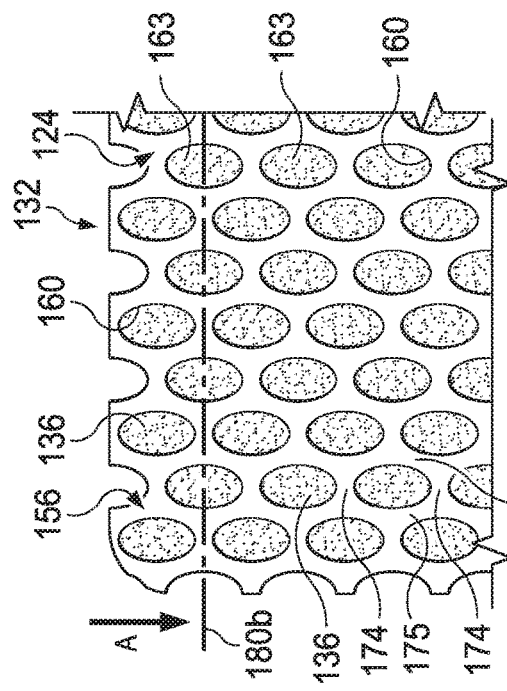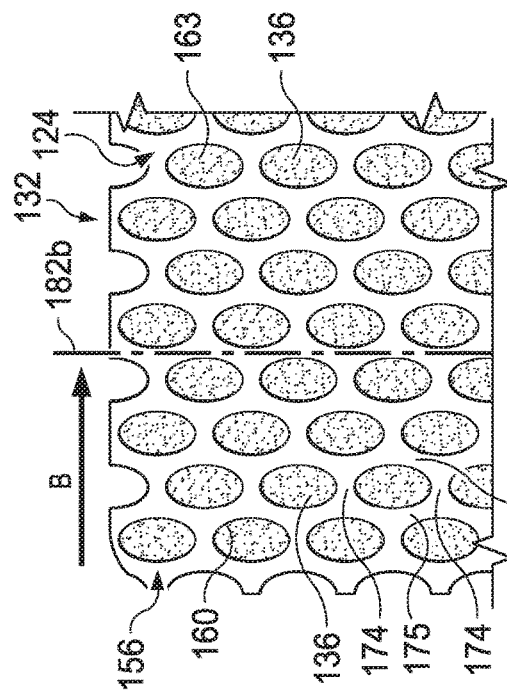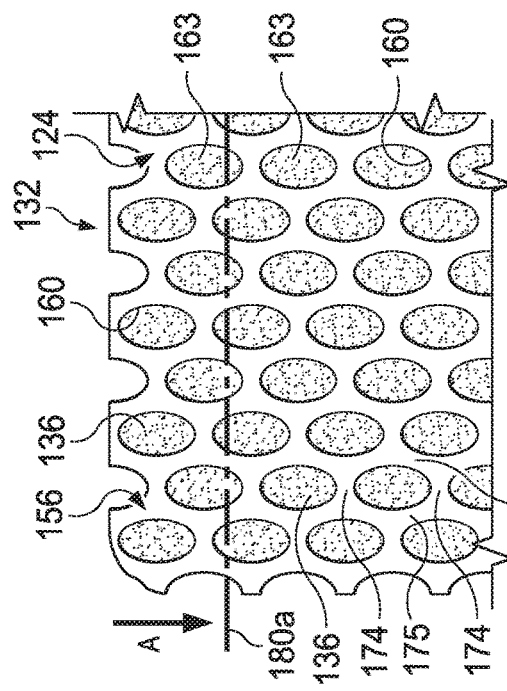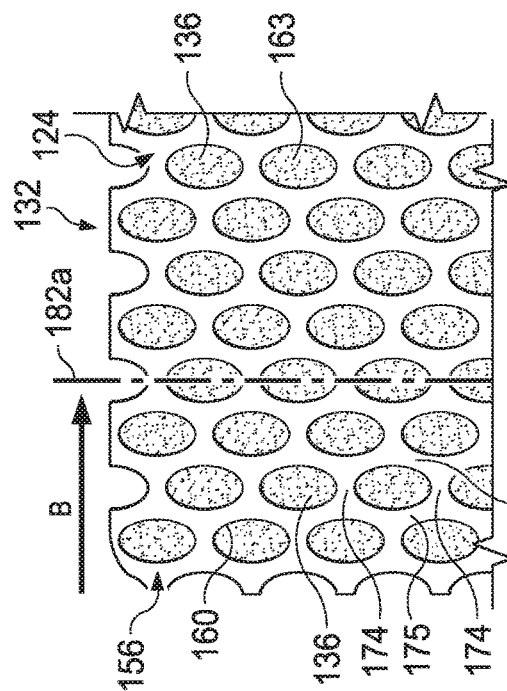

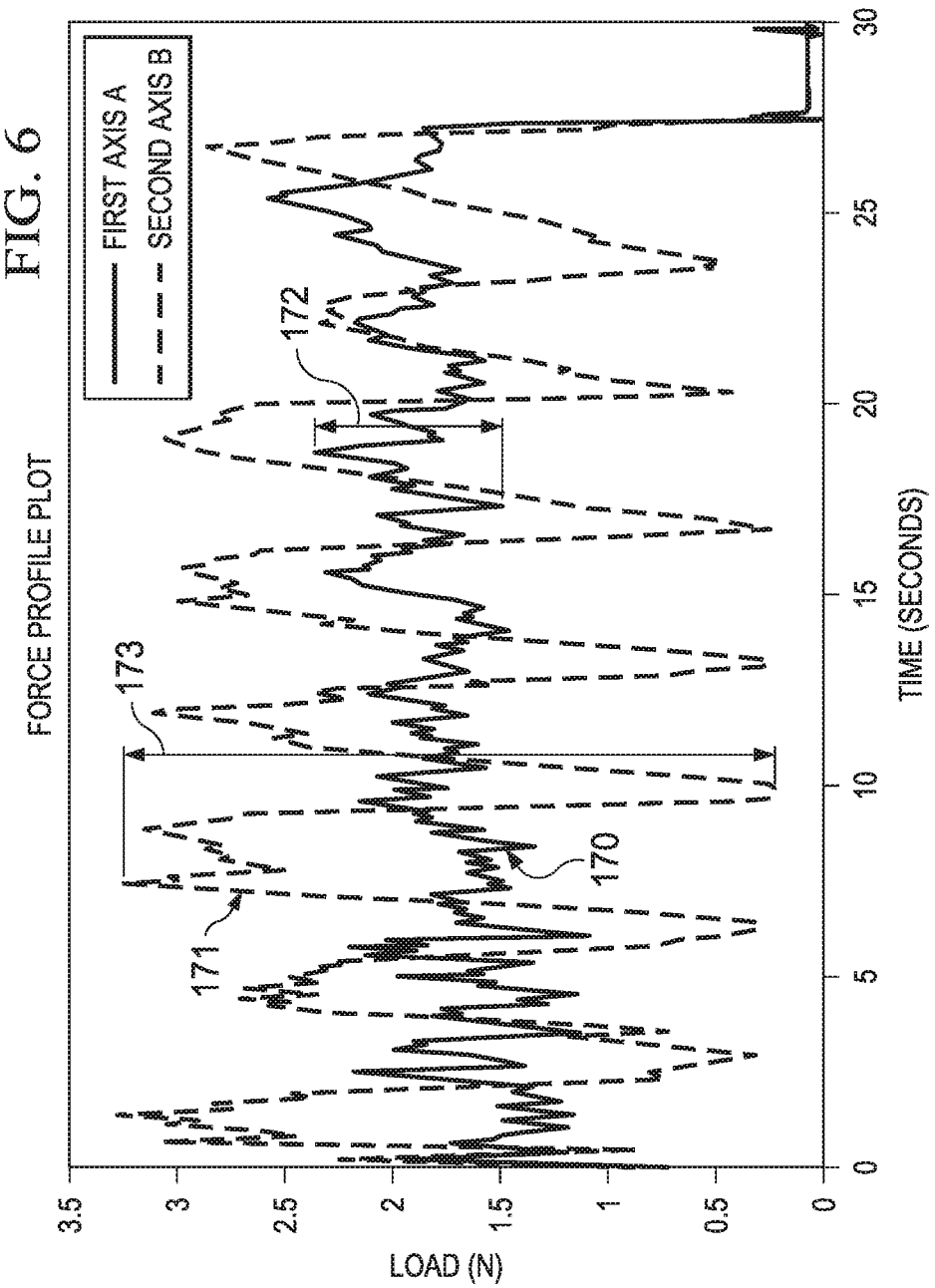

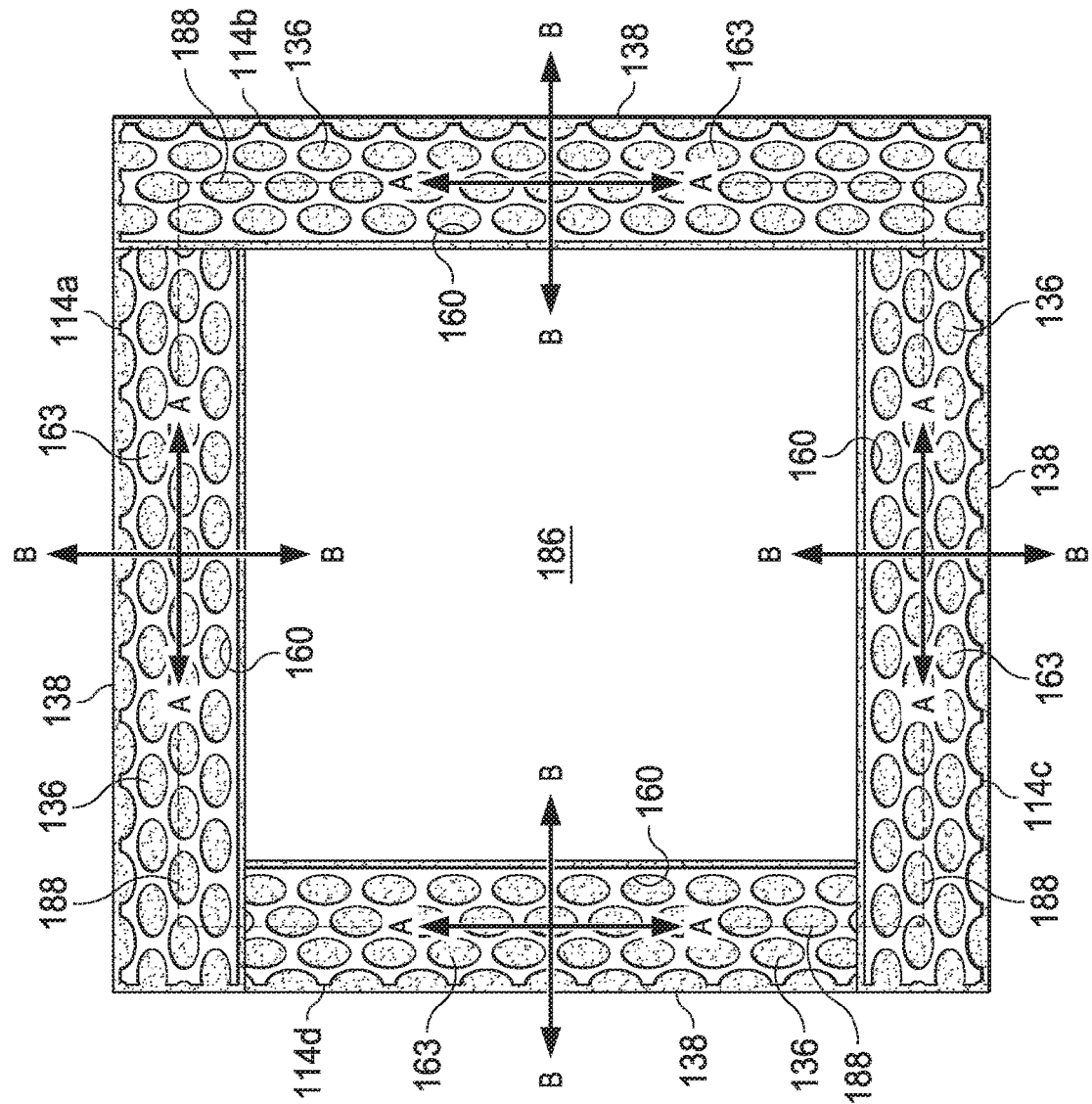

MEDICAL DRAPES AND METHODS FOR REDUCING TRAUMA ON REMOVAL

RELATED APPLICATION

This application is a divisional of U.S. patent application Ser. No. 15/341,857, entitled "Medical Drapes and Methods for Reducing Trauma on Removal," filed Nov. 2, 2016, which claims the benefit, under 35 USC 119(e), of the filing of U.S. Provisional Patent Application No. 62/257,082, entitled "Medical Drapes and Methods for Reducing Trauma on Removal," filed Nov. 18, 2015, which is incorporated herein by reference for all purposes.

TECHNICAL FIELD

This disclosure relates generally to medical treatment systems and, more particularly, but not by way of limitation, to medical drapes, systems, devices, and methods for treating a tissue site.

BACKGROUND

A medical drape may have a variety of applications alone or in combination with medical treatment systems, devices, and methods that may be useful for treating a tissue site. Improvements to medical drapes, systems, devices, and methods may benefit manufacturers, healthcare providers, and patients. Such benefits may include, without limitation, faster healing times, increased patient comfort, and enhanced efficiency and usability.

SUMMARY

According to some illustrative, non-limiting examples, a medical drape for treating a tissue site may include an adherent surface including first adherent force profile oriented along a first axis and a second adherent force profile oriented along a second axis. The first adherent force profile may have an average force less than an average force of the second adherent force profile.

According to some illustrative, non-limiting examples, a medical drape for treating a tissue site may include an adhesive pattern on an adherent surface. The adherent surface may include a first adherent force profile oriented along a first axis and a second adherent force profile oriented along a second axis. The first adherent force profile may have an average force less than an average force of the second adherent force profile.

According to some illustrative, non-limiting examples, a system for treating a tissue site may include a medical drape adapted to provide a sealed space relative to the tissue site. The medical drape may include an adherent surface including first adherent force profile oriented along a first axis and a second adherent force profile oriented along a second axis. The first adherent force profile may have an average force less than an average force of the second adherent force profile. The system may additionally include a manifold and a reduced-pressure source. The manifold may be adapted to be disposed in the sealed space and to distribute reduced pressure to the tissue site. The reduced-pressure source may be for fluidly coupling to the sealed space.

According to some illustrative, non-limiting examples, a medical drape for treating a tissue site may include a base layer and an adhesive. The base layer may include a first axis, a second axis, and a plurality of apertures positioned on the base layer. The plurality of apertures may include an elongate length and a width positioned normal to the elongate length. The elongate length may be oriented along the first axis and configured to overlap at least a portion of a space between the plurality of apertures along the first axis. The plurality of apertures may be separated by a border region along the second axis. The adhesive may be carried by the plurality of apertures.

According to some illustrative, non-limiting examples, a system for treating a tissue site with reduced pressure may include a manifold, a cover, a medical drape, and a reduced-pressure source. The manifold may be adapted to distribute reduced pressure to the tissue site. The manifold may include a tissue-facing side for facing the tissue site, and an outward-facing side opposite the tissue-facing side. The cover may be adapted to be positioned on the outward-facing side of the manifold. In some embodiments, the cover may provide a sealed space at the tissue site containing the manifold. Further, the cover may include a periphery. The medical drape may be adapted to be positioned proximate to the periphery of the cover. The medical drape may include an adherent surface including an average adherent force along a first axis of the medical drape that is less than an average adherent force along a second axis of the medical drape. The first axis may be oriented along the periphery of the cover. The reduced-pressure source may be adapted for positioning in fluid communication with the sealed space.

According to some illustrative, non-limiting examples, a method for treating a tissue site may include disposing a manifold proximate to the tissue site and covering the manifold at the tissue site with a cover. Further, the method may include providing a medical drape. The medical drape may include an adherent surface including an average adherent force along a first axis of the medical drape that is less than an average adherent force along a second axis of the medical drape. Further, the method may include positioning the adherent surface of the medical drape on tissue around a periphery of the cover. The first axis of the medical drape may be oriented along the periphery of the cover.

According to some illustrative, non-limiting examples, a method for treating a tissue site may include providing a medical drape adhered to a tissue at the tissue site. The medical drape may include an adherent surface including an average adherent force along a first axis of the medical drape that is less than an average adherent force along a second axis of the medical drape. Further, the method may include removing the medical drape from the tissue. Removing the medical drape may include peeling the medical drape away from the tissue along the first axis of the medical drape.

According to some illustrative, non-limiting examples, a medical drape for treating a tissue site may include a base layer and an adhesive. The base layer may include a first axis, a second axis, and a plurality of apertures on the base layer. At least one of the plurality of apertures may be configured to overlap at least a portion of a space between the plurality of apertures along the first axis. The plurality of apertures may be separated along the second axis by a border region. The adhesive may be adapted to be carried by the plurality of apertures.

According to some illustrative, non-limiting examples, a medical drape for treating a tissue site may include a first adhesive layer and a second adhesive. The first adhesive layer may include a first axis, a second axis, and a plurality of apertures disposed through the first adhesive layer in an overlapping pattern. The plurality of apertures may include an elongate length and a width positioned normal to the elongate length. The elongate length may be oriented along the first axis and configured to overlap a at least a portion of a space between the plurality of apertures along the first axis. The plurality of apertures may be separated by a border region along the second axis. The second adhesive may be carried by the plurality of apertures, and may include a second adherent force greater than a first adherent force of the first adhesive layer. The first adhesive layer and the second adhesive may define an adhesive pattern on an adherent surface. The adherent surface may include a first adherent force profile oriented along the first axis and a second adherent force profile oriented along the second axis. The first adherent force profile may have an average force less than an average force of the second adherent force profile.

Other aspects, features, and advantages of the illustrative embodiments will become apparent with reference to the drawings and detailed description that follow.

BRIEF DESCRIPTION OF THE DRAWINGS

FIGS. 5A-5B each depict an illustrative datum line that may correspond to part of an example adherent force profile along a first axis for a medical drape according to this disclosure;

FIGS. 5C-5D each depict an illustrative datum line that may correspond to part of an example adherent force profile along a second axis for a medical drape according to this disclosure;

FIG. 6 is a graphical plot of load versus time of an example adherent force profile along a first axis and an example adherent force profile along a second axis for a medical drape according to this disclosure;

FIG. 7 is a plan view of an illustrative example of a plurality of example medical drapes deployed with an illustrative example of a cover.

DETAILED DESCRIPTION OF ILLUSTRATIVE EMBODIMENTS

In the following detailed description of illustrative examples or embodiments, reference is made to the accompanying drawings that form a part of this disclosure. Other embodiments may be used, and logical, structural, mechanical, electrical, and chemical changes may be made without departing from the scope of this disclosure. Further, the description may omit certain information known to those skilled in the art. Therefore, the following detailed description is non-limiting, with the scope of the illustrative embodiments being defined by the appended claims. Further, as used throughout this disclosure, "or" does not require mutual exclusivity.

In one embodiment, described below, the medical drape described herein may be used as part of a system for treating wounds. Such systems can include absorbent materials for managing exudates or negative pressure wound therapy systems. In other embodiments the medical drape may be used as a stand along device.

Figure 1:
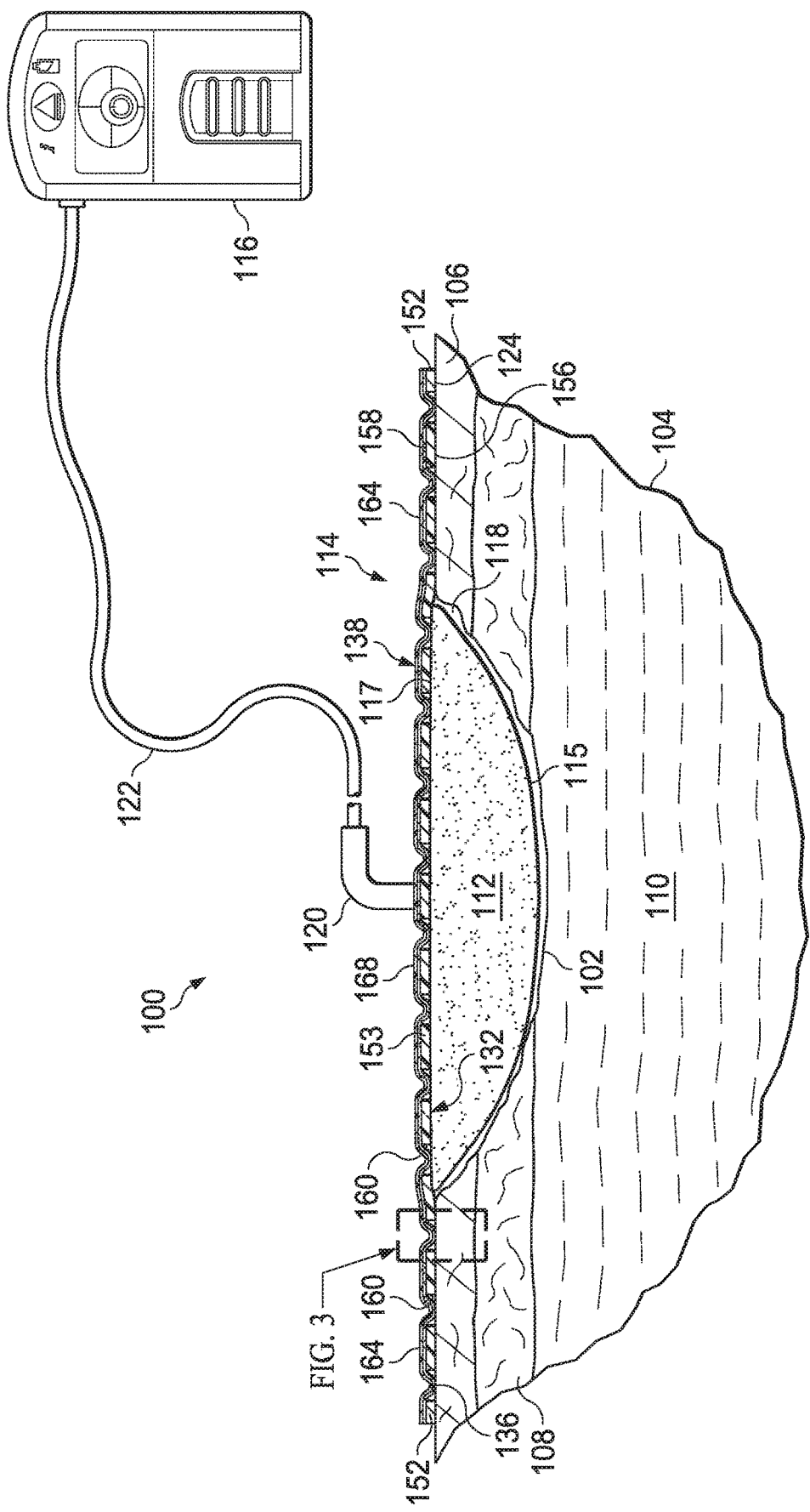
FIG. 1 is a partial cut-away view of an illustrative example of a system suitable for treating a tissue site.
Figure 2:
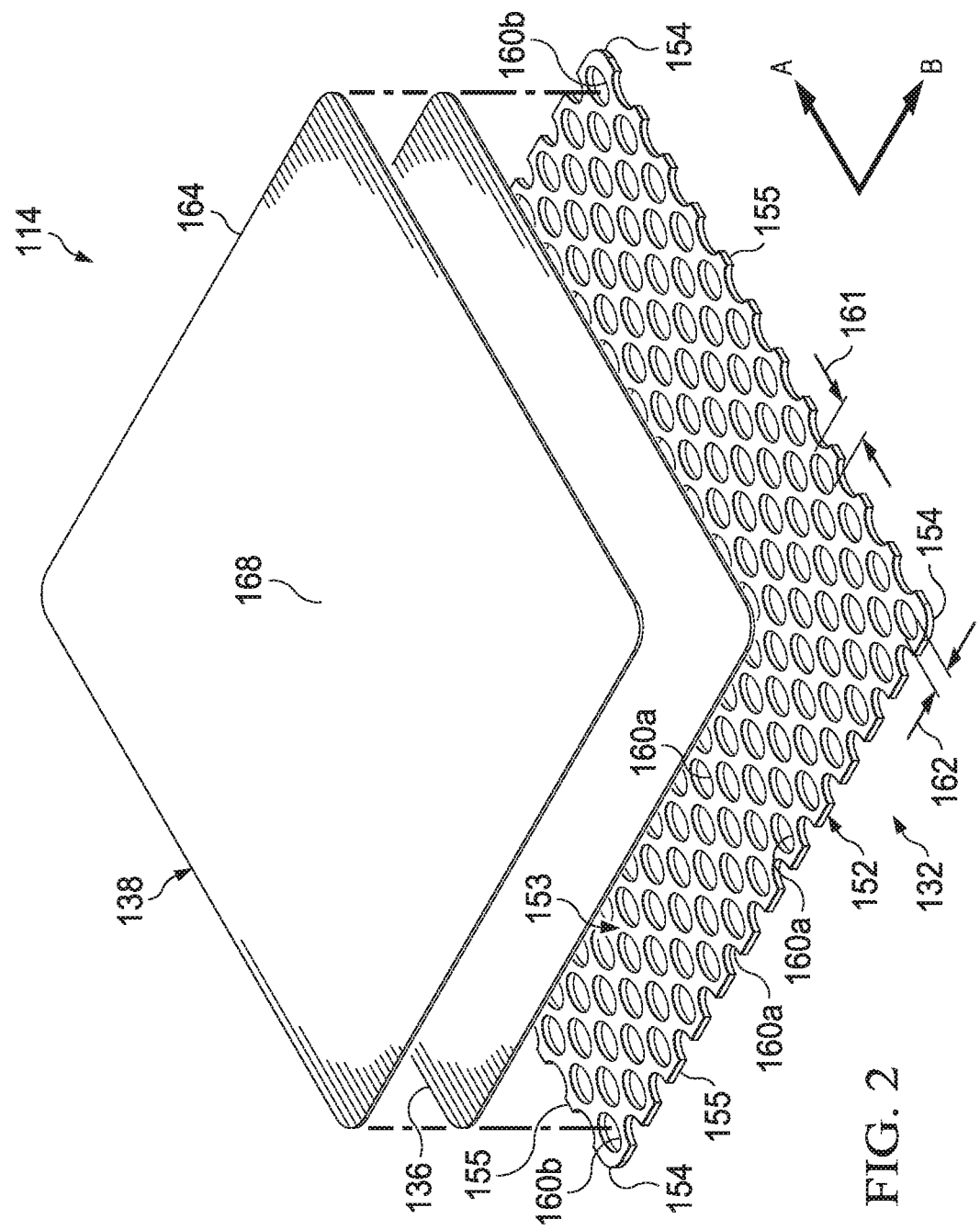
FIG. 2 is an exploded perspective view of an illustrative example of a medical drape that may be deployed with the example system in FIG. 1.

Referring to FIG. 1, provided is an illustrative, non-limiting embodiment of a system 100 suitable for treating a tissue site 102 on a patient 104. The tissue site 102 is shown extending through or involving an epidermis 106, a dermis 108, and a subcutaneous tissue 110. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 102 may include removal of fluids, such as, for example, exudate or ascites. The system 100 may also be used with other tissue sites without limitation, and may be used with or without reduced pressure.

In some embodiments, the system 100 may include a manifold 112, a medical drape 114, and a reduced-pressure source 116. The manifold 112 may be disposed proximate to the tissue site 102, and may include a tissue-facing side 115 for facing the tissue site 102 and an outward-facing side 117 opposite the tissue-facing side 115. Further, the manifold 112 may be adapted to distribute reduced pressure to the tissue site 102, or otherwise manage fluids that may be associated with the tissue site 102. The medical drape 114 may be adapted to provide a sealed space 118 relative to the tissue site 102. For example, the medical drape 114 may cover or be disposed over the manifold 112 to form the sealed space 118. The manifold 112 may be positioned or disposed in the sealed space 118, and the reduced-pressure source 116 may be positioned or coupled in fluid communication with the manifold 112 or the sealed space 118.

The manifold 112 may be a substance or structure provided to assist in applying reduced pressure to, delivering fluids to, or removing fluids from the tissue site 102. The manifold 112 may include a plurality of flow channels or pathways that can distribute fluids provided to and removed from the tissue site 102. In some embodiments, these flow channels or pathways may be interconnected to improve distribution of fluids provided to or removed from the tissue site 102. Further, in some embodiments, the manifold 112 may comprise one or more of the following: a biocompatible material capable of being placed in contact with the tissue site 102 and distributing reduced pressure to the tissue site 102; devices that have structural elements arranged to form flow channels, such as, for example, cellular foam, open-cell foam, porous tissue collections, liquids, gels, and foams that include, or cure to include, flow channels; porous material, such as foam, gauze, felted mat, or any other material suited to a particular biological application; or porous foam that includes a plurality of interconnected cells or pores that act as flow channels, such as a polyurethane, open-cell, reticulated foam manufactured as GranuFoam® by Kinetic Concepts, Incorporated of San Antonio, Tex.; a bioresorbable material; or a scaffold material. In some embodiments, the manifold 112 may also be used to distribute fluids such as medications, anti-bacterials, growth factors, and various solutions to the tissue site 102.

The reduced-pressure source 116 may provide reduced pressure as a part of the system 100. The reduced-pressure source 116 may be fluidly coupled to a conduit interface 120 by a delivery conduit 122. An aperture (not shown) may be formed on a portion of the medical drape 114 to allow fluid communication between the sealed space 118 and the reduced-pressure source 116 through the conduit interface 120 and the delivery conduit 122.

As used herein, "reduced pressure" may refer to a pressure less than the ambient pressure at a tissue site being subjected to treatment, such as the tissue site 102. The reduced pressure may be less than the atmospheric pressure. The reduced pressure may also be less than a hydrostatic pressure at a tissue site. Unless otherwise indicated, quantitative values of pressure stated herein are gauge pressures.

The reduced pressure delivered to the sealed space 118 or the manifold 112 may be constant or varied, patterned or random, and may be delivered continuously or intermittently. Although the terms "vacuum" and "negative pressure" may be used to describe the pressure applied to a tissue site, the actual pressure applied to the tissue site may be more than the pressure normally associated with a complete vacuum. Consistent with the use herein, unless otherwise indicated, an increase in reduced pressure or vacuum pressure may refer to a relative reduction in absolute pressure.

The reduced-pressure source 116 may be any device for supplying a reduced pressure, such as a vacuum pump, wall suction, micro-pump, or other source. While the amount and nature of reduced pressure applied to a tissue site may vary according to the application, the reduced pressure may be, for example, between about −5 mm Hg (−667 Pa) to about −500 mm Hg (−66.7 kPa). In some embodiments, the reduced pressure may be between about −75 mm Hg (−9.9 kPa) to about −300 mm Hg (−39.9 kPa). Further, in some embodiments, the reduced pressure may be between about −75 mm Hg (−9.9 kPa) to about −200 mm Hg (−26.66 kPa).

The reduced pressure developed by the reduced-pressure source 116 may be delivered through the delivery conduit 122 to the conduit interface 120. The conduit interface 120 may allow the reduced pressure to be delivered through the medical drape 114 to the manifold 112 and the sealed space 118. In some embodiments, the conduit interface 120 may be a T.R.A.C.® Pad or Sensa T.R.A.C.® Pad available from KCI of San Antonio, Tex. In other embodiments, the conduit interface 120 may be omitted, and the delivery conduit 122 may be inserted through the medical drape 114 to provide fluid communication with the sealed space 118. Further, in other embodiments, the reduced pressure may also be generated by a device, such as, for example, a micro-pump that may be coupled directly to the medical drape 114 or the manifold 112 without use of the delivery conduit 122 or the conduit interface 120.

Referring to FIGS. 1-4, the medical drape 114 may include an adherent surface 124 adapted to face the tissue site 102. The medical drape 114 may be configured to provide a fluid seal over, around, or relative to the tissue site 102. Further, the medical drape 114 may allow vapor to egress from the tissue site 102 through the medical drape 114. For example, in some embodiments, the medical drape 114 may be sized or configured to cover the tissue site 102 and a tissue around or surrounding the tissue site 102, such as, for example, the epidermis 106 of the patient 104. In some embodiments, the medical drape 114 may entirely or completely cover the tissue site 102. In other embodiments, the medical drape 114 may be used on or at a portion of the tissue site 102, or with other components of the system 100, in a variety of applications. For example, the medical drape 114 may be used, without limitation, to provide or to enhance a fluid seal, to support tissue or system components, or to connect tissue or system components.

In some embodiments, the medical drape 114 may include a base layer 132 and an adhesive 136. In some embodiments, the base layer 132 may be referred to as a first adhesive layer 132 and the adhesive 136 may be referred to as a second adhesive 136 or a second adhesive layer 136. As further described herein, the base layer 132 or the first adhesive layer 132 may have a first adherent force, and the adhesive 136 or the second adhesive 136 may have a second adherent force that is different from the first adherent force. For example, in some embodiments, the second adherent force of the second adhesive 136 may be greater than the first adherent force of the first adhesive layer 132. A material having a greater adherent force or adherency may refer to a greater ability or force associated with the material being able to stick, attract, tack, or hold on to another object. Thus, in some embodiments, the second adhesive 136 may have a greater holding force than the first adhesive layer 132.

Further, in some embodiments, the medical drape 114 may include an optional sealing member 138. The sealing member 138 may, without limitation, enhance the fluid seal of the medical drape 114 relative to the tissue site 102 and assist with deployment of the adhesive 136.

The base layer 132 may include a base layer flange portion 152 that may be configured to extend beyond a periphery or lateral boundary of the tissue site 102 or the manifold 112, for example, for coupling to tissue around or surrounding the tissue site 102 or the manifold 112. In some embodiments, the base layer flange 152 may be configured to be positioned in direct contact with tissue around or surrounding the tissue site 102, such as the epidermis 106. Further, in some embodiments, the base layer flange 152 may be positioned around or surrounding a central region 153 of the base layer 132. Thus, in some embodiments, the base layer flange 152 may define, form, or be positioned at, a periphery of the base layer 132. Further, the base layer flange 152 may be configured to be positioned around the periphery of the manifold 112 and the periphery of the tissue site 102. In some embodiments, the base layer flange 152 may be configured to substantially or entirely surround the periphery of the manifold 112 and the periphery of the tissue site 102.

Further, the base layer 132 may include corners 154 and edges 155. The corners 154 and the edges 155 may be part of the base layer flange 152. One of the edges 155 may meet another of the edges 155 to define one of the corners 154.

In some embodiments, the base layer 132 may include a first side 156, a second side 158 opposite the first side 156, and a plurality of apertures 160 or perforations. Further, the base layer 132 may define a first axis A of the medical drape 114 and a second axis B of the medical drape 114. The first side 156 of the base layer 132 may carry, support, or define the adherent surface 124 of the medical drape 114. In some embodiments, the plurality of apertures 160 may be positioned on the base layer 132. In such embodiments, the plurality of apertures 160 may be configured as pockets or depressions that may not pass entirely through a thickness of the base layer 132, or between the first side 156 and the second side 158 of the base layer 132. For example, the base layer 132 may be a sheet or carrier layer adapted to carry the adhesive 136 on the first side 156 of the base layer 132 in an adhesive pattern as described herein, such as, without limitation, as a pattern of adhesive dots, ovals, rectangles, or other shapes. In other embodiments, the plurality of apertures may be disposed through the base layer 132 between the first side 156 and the second side 158.

In some embodiments, the apertures 160 may be positioned at the central region 153 of the base layer 132, for example, to facilitate fluid communication with the manifold 112 or to couple the base layer 132 to the manifold 112. Further, in some embodiments, the apertures 160 may be positioned at the base layer flange 152, for example, to facilitate coupling the base layer 132 to tissue around or surrounding the tissue site 102. Further, in some embodiments, the central region 153 of the base layer 132 may be positioned adjacent to or proximate to the manifold 112, and the base layer flange 152 may be positioned adjacent to or proximate to tissue around or surrounding the tissue site 102. In this manner, the base layer flange 152 may be positioned around or surrounding the manifold 112. Further, the apertures 160 in the base layer 132 may be in fluid communication with the manifold 112 and tissue around or surrounding the tissue site 102.

The apertures 160 in the base layer 132 may have any shape, such as, for example, circles, squares, stars, ovals, polygons, slits, complex curves, rectilinear shapes, triangles, diamonds, or other shapes. The apertures 160 may be formed by cutting, by application of local RF energy, or other suitable techniques for forming an opening. Each of the apertures 160 of the plurality of apertures 160 may have an area and a boundary dimension. For example, the area of each of the apertures 160 may refer to an open space, open region, or footprint defining each of the apertures 160. The boundary dimension is a measurement of the size of an aperture and may be, for example, a diameter, a width, a length or other distance between two opposing boundaries of one of the apertures 160. The boundary dimension of each of the apertures 160 may be used to determine or define the area of each of the apertures 160. The area of the apertures 160 described in the illustrative embodiments herein may be substantially similar to the area in other embodiments (not shown) for the apertures 160 that may have non-circular shapes.

In some embodiments, the plurality of apertures 160 may have an elongate shape and include an elongate length 161 and a width 162 arranged or positioned normal to the elongate length 161. In some embodiments, the elongate length 161 may be arranged at an angle relative to the width 162. In such embodiments, the elongate length 161 may be greater than the width 162. A suitable elongate shape may be, without limitation, an oval, rectangle, or diamond. In some embodiments, the plurality of apertures 160 may have an aspect ratio between about 1.2 to about 1.8. The aspect ratio of the plurality of apertures 160 may be determined or defined by comparing or dividing the elongate length 161 by the width 162. Further, in some embodiments, the elongate length 161 may be between about 20 percent to about 80 percent greater than the width 162. The boundary dimension for embodiments of the plurality of apertures 160 including an elongate shape may be the elongate length 161.

The size and shape of each of the apertures 160 may be substantially the same or may vary depending on the position of the aperture 160 in the base layer 132. Similarly, the boundary dimension of each of the apertures 160 may be substantially the same, or each boundary dimension may vary depending, for example, on the position of the aperture 160 in the base layer 132. For example, the boundary dimension of the apertures 160 in the base layer flange 152 may be larger than the boundary dimension of the apertures 160 in the central region 153 of the base layer 132. The boundary dimension of each of the apertures 160 may be between about 1 millimeter to about 50 millimeters. In some embodiments, the boundary dimension of each of the apertures 160 may be between about 1 millimeter to about 20 millimeters. The apertures 160 may have a uniform pattern or may be randomly distributed on the base layer 132. Further, in some embodiments, an aperture 160$b$ positioned at the corners 154 may be smaller than an aperture 160$a$ positioned in other portions of the base layer 132, such as the base layer flange 152 or the central region 153. In some embodiments, the apertures 160$a$ may have a boundary dimension between about 9 millimeters to about 11 millimeters, and the apertures 160$b$ may have a boundary dimension between about 7 millimeters to about 9 millimeters.

The base layer 132 may be a soft, pliable material. For example, the base layer 132 may comprise a gel, a silicone, hydrocolloid, hydrogel, polyurethane gel, polyolefin gel, hydrogenated styrenic copolymer gels, a foamed gel, a soft closed cell foam such as polyurethanes and polyolefins coated with an adhesive described below, polyurethane, polyolefin, or hydrogenated styrenic copolymers. The base layer 132 may have a thickness between about 500 microns ($\mu$m) and about 1000 microns ($\mu$m). In some embodiments, the base layer 132 may have a stiffness between about 5 Shore OO to about 80 Shore OO. The base layer 132 may be comprised of hydrophobic or hydrophilic materials. The base layer 132 may be operable to enhance a fluid seal with the tissue site 102 as described herein.

Figure 3:
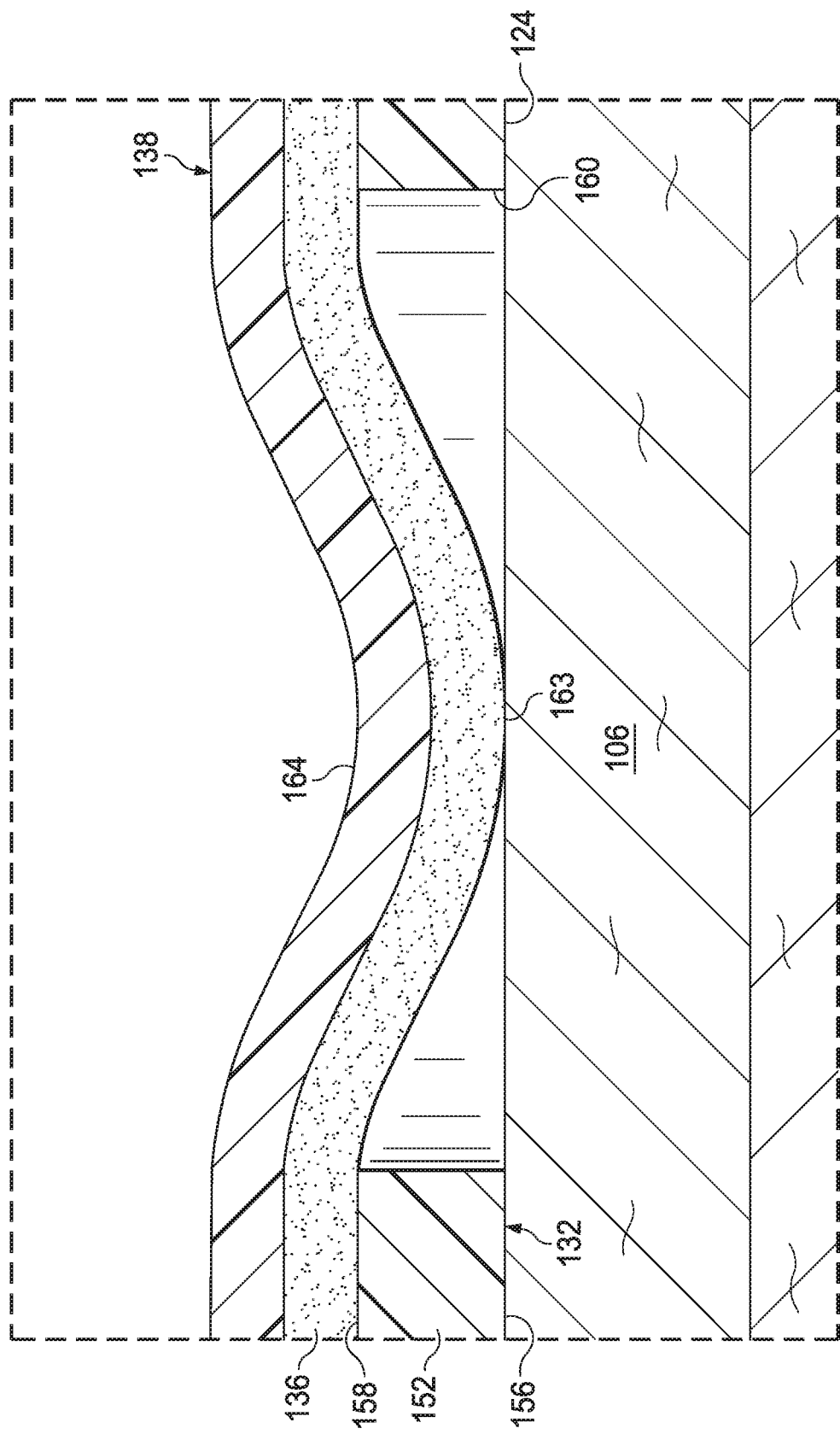
FIG. 3 is a detail view of an illustrative example of a medical drape taken at reference FIG. 3 shown in FIG. 1.

In some embodiments, the adhesive 136 may be associated with the apertures 160 such the adhesive 136 may be configured to extend, flow, flex, deform, or be pressed into or through the apertures 160. In some embodiments, the adhesive 136 may be configured to extend, flow, flex, deform, or be pressed outward from the apertures 160. As such, the adhesive 136 may be exposed to, positioned in contact with, positioned adjacent to, or positioned in fluid communication with the apertures 160 and tissue surrounding the tissue site 102 through the apertures 160. As shown in FIG. 3, in some embodiments, the adhesive 136 may extend, flow, flex, deform, or be pressed through the plurality of apertures 160 to form one or more adherent couplings 163 on the adherent surface 124 of the medical drape 114. For example, in some embodiments, the adhesive 136 may be initially positioned on the second side 158 of the base layer 132 and adapted to extend, flow, flex, deform, or be pressed through the plurality of apertures 160 to the first side 156 to form the adherent couplings 163 on the adherent surface 124. Further, in some embodiments, the adhesive 136 may be initially positioned on the first side 156 of the base layer 132 and carried or supported by the plurality of apertures 160 on the first side 156 to form the adherent couplings 163. Thus, in some embodiments, the adherent couplings 163 may be portions or dots of the adhesive 136 arranged on the first side 156 of the base layer 132 in an adhesive pattern. The adherent couplings 163 may be spaced apart from one another on the adherent surface 124 such that at least a portion of the adherent surface 124 is free of the adherent couplings 163. The adherent couplings 163 may have a greater adherent force than the portion of the adherent surface 124 that is free of the adherent couplings 163.

The adherent couplings 163 may define at least a portion of the adherent surface 124 of the base layer 132. Further, the arrangement or positioning of the adherent couplings 163 described herein may define an adhesive pattern 165 on the base layer 132, such as, for example, on the adherent surface 124 of the base layer 132. In some embodiments, the plurality of apertures 160 and the adhesive 136 may define the adherent couplings 163, and therefore, the plurality of apertures 160 and the adhesive 136 may also define the adherent surface 124 of the base layer 132. However, the scope of this disclosure is not limited to any particular features described herein for forming the adherent couplings 163.

The adherent couplings 163 may contact the epidermis 106 for securing the medical drape 114 to, for example, tissue around or surrounding the tissue site 102. The adherent couplings 163 may also contact other tissue or other components of the system 100 as desired. Each of the adherent couplings 163 may correspond to each of the plurality of apertures 160, and may have substantially the same position, orientation, configuration, spacing, or shape as the plurality of apertures 160. Thus, the adherent couplings 163 may have substantially the same boundary dimension as the plurality of apertures 160, including, for example, substantially the same elongate length 161, width 162, and orientation. Further, in some embodiments, the adherent couplings 163 may have an aspect ratio between about 1.2 to about 1.8 similar to the plurality of apertures 160. Accordingly, such features may be interchangeably referred to herein as being associated with the plurality of apertures 160 or the adherent couplings 163. Further, in some embodiments, the plurality of apertures 160 may provide a corresponding plurality of the adherent couplings 163 positioned on the adherent surface 124. The plurality of apertures 160 may provide sufficient contact of the adhesive 136, forming the adherent couplings 163, to the epidermis 106 to secure the medical drape 114 about the tissue site 102. However, the configuration of the apertures 160 and the adhesive 136, described below, may permit release and repositioning of the dressing assembly 112 about the tissue site 102.

At least one of the apertures 160a in the base layer flange 152 may be positioned at the edges 155 and may have an interior open or exposed at the edges 155 such that the edge defines one or more sides of the aperture. Thus, the exposed interior of the apertures 160a at the edges 155 may permit the adhesive 136 to extend to the edge of the dressing.

The size and configuration of the apertures 160 may be designed to control the adherence of the medical drape 114 at the tissue site 102. For example, the size and number of the apertures 160b in the corners 154 may be adjusted as necessary, depending on the chosen geometry of the corners 154, to increase the exposed surface area of the adhesive 136 compared to the central region 153. Further, the apertures 160b at the corners 154 may be fully housed within the base layer 132, substantially precluding fluid communication in a lateral direction exterior to the corners 154. The apertures 160b at the corners 154 being fully housed or enclosed within the perimeter of the base layer 132 may substantially preclude fluid communication of the adhesive 136 exterior to the corners 154, and may provide improved handling. Further, the immediate outer perimeter of the drape being substantially free of the adhesive 136 may increase the flexibility of the corners 154 to enhance comfort. Similar to the apertures 160b in the corners 154, any of the apertures 160 may be adjusted in size and number to increase the surface area of the adhesive 136 in fluid communication through the apertures 160 for a particular application or geometry of the base layer 132.

The adhesive 136 may be a medically-acceptable adhesive. For example, the adhesive 136 may comprise an acrylic adhesive, rubber adhesive, high-tack silicone adhesive, polyurethane, or other adhesive substance. In some embodiments, the adhesive 136 may be a pressure-sensitive adhesive comprising an acrylic adhesive with coating weight of 15 grams/m$^2$ (gsm) to 70 grams/m$^2$ (gsm). In some embodiments, the adhesive 136 may be a layer having substantially the same shape as the base layer 132. In some embodiments, the adhesive 136 may be continuous layer. In other embodiments, the adhesive 136 may be discontinuous. For example, the adhesive 136 may be a patterned coating on a carrier layer, such as, for example, a side of the sealing member 116 adapted to face the epidermis 106. Further, discontinuities in the adhesive 136 may be sized to control the amount of the adhesive 136 extending through the apertures 160 in the base layer 132 to reach the epidermis 106. The discontinuities in the adhesive 136 may also be sized to enhance the Moisture Vapor Transfer Rate (MVTR) of the medical drape 114.

Factors that may be used to control the adhesion strength of the medical drape 114 may include the size of the boundary dimension, the size of the area, and the number of the apertures 160 in the base layer 132; the thickness of the base layer 132; the thickness and amount of the adhesive 136; and the tackiness of the adhesive 136. An increase in the amount of the adhesive 136 extending through the apertures 160 may correspond to an increase in the adhesion strength of the medical drape 114. A decrease in the thickness of the base layer 132 may correspond to an increase in the amount of adhesive 136 extending through the apertures 160. Thus, the boundary dimension and configuration of the apertures 160, the thickness of the base layer 132, and the amount and tackiness of the adhesive 136 utilized may be varied to provide a desired adhesion strength for the medical drape 114. In some embodiments, the thickness of the base layer 132 may be about 200 microns, the adhesive 136 may have a thickness of about 30 microns and a tackiness of 2000 grams per 25 centimeter wide strip, and the boundary dimension of the apertures 160a in the base layer 132 may be about 10 millimeters.

In some embodiments, the tackiness of the adhesive 136 may vary in different locations of the base layer 132. For example, in locations of the base layer 132 where the apertures 160 are comparatively large, such as the apertures 160a, the adhesive 136 may have a lower tackiness than other locations of the base layer 132 where the apertures 160 are smaller, such as the apertures 160b. In this manner, locations of the base layer 132 having larger apertures 160 and lower tackiness adhesive 136 may have an adhesion strength comparable to locations having smaller apertures 160 and higher tackiness adhesive 136.

The sealing member 138 may be adapted to partially or entirely cover the base layer 132, such as the second side 158 of the base layer 132. For example, in some embodiments, the sealing member 138 may have a periphery 164 and a central region 168. The periphery 164 of the sealing member 138 may be positioned proximate to the base layer flange 152. In some embodiments, the adhesive 136 may be positioned at least between the periphery 164 of the sealing member 138 and the base layer flange 152. In some embodiments, a portion of the periphery 164 of the sealing member 138 may extend beyond the base layer flange 152 and into direct contact with tissue around or surrounding the tissue site 102. Thus, the adhesive 136 may also be positioned at least between the periphery 164 of the sealing member 138 and tissue, such as the epidermis 106, surrounding the tissue site 102. In some embodiments, the adhesive 136 may be disposed on a surface of the sealing member 138 adapted to face the tissue site 102 and the base layer 132.

In some embodiments, the sealing member 138 may be configured to extend beyond the periphery of the manifold 112. Further, in some embodiments, the sealing member 138 may be configured to cover at least a portion of the manifold 112 and to extend beyond the periphery of the manifold 112 proximate to the base layer flange 152. In some embodiments, the adhesive 136 may be positioned between the sealing member 138 and the base layer 132 such that the adhesive 136 may be adapted to flow through the plurality of apertures 160 when a force is applied to an exterior surface of the sealing member 138 to form the adherent couplings 163 on the first side 156 of the base layer 132.

The initial tackiness of the base layer 132 may be sufficient to initially couple the base layer 132 to the epidermis 106, the manifold 112, or other component of the system 100. Once in a desired position, a force may be applied to an exterior surface of the sealing member 138 to secure the medical drape 114 in place. For example, a caretaker may rub the exterior surface of the sealing member 138, which may cause at least a portion of the adhesive 136 to move or deform into or through the plurality of apertures 160 for forming and positioning the adherent couplings 163 in contact with tissue, such as the epidermis 106, or components of the system 100. The adherent couplings 163 may provide a secure and releasable mechanical fixation.

The sealing member 138 may be formed from any material that allows for a fluid seal. A fluid seal may be a seal adequate to maintain reduced pressure at a desired site given the particular reduced pressure source or system involved. In some embodiments, the sealing member 138 may be, without limitation, a liquid impermeable material or film. Further, in some embodiments, the sealing member 138 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; Expopack 2327; or other appropriate material.

The sealing member 138 may be vapor permeable and liquid impermeable, thereby allowing vapor and inhibiting liquids from exiting the sealed space 118. In some embodiments, the sealing member 138 may be a flexible, breathable film, membrane, or sheet having a high moisture vapor transfer rate (MVTR) of, for example, at least about 300 g/m$^2$ per 24 hours. In other embodiments, a low or no vapor transfer drape might be used. The sealing member 138 may comprise a range of medically suitable films having a thickness between about 15 microns (μm) to about 50 microns (μm).

Figure 4:
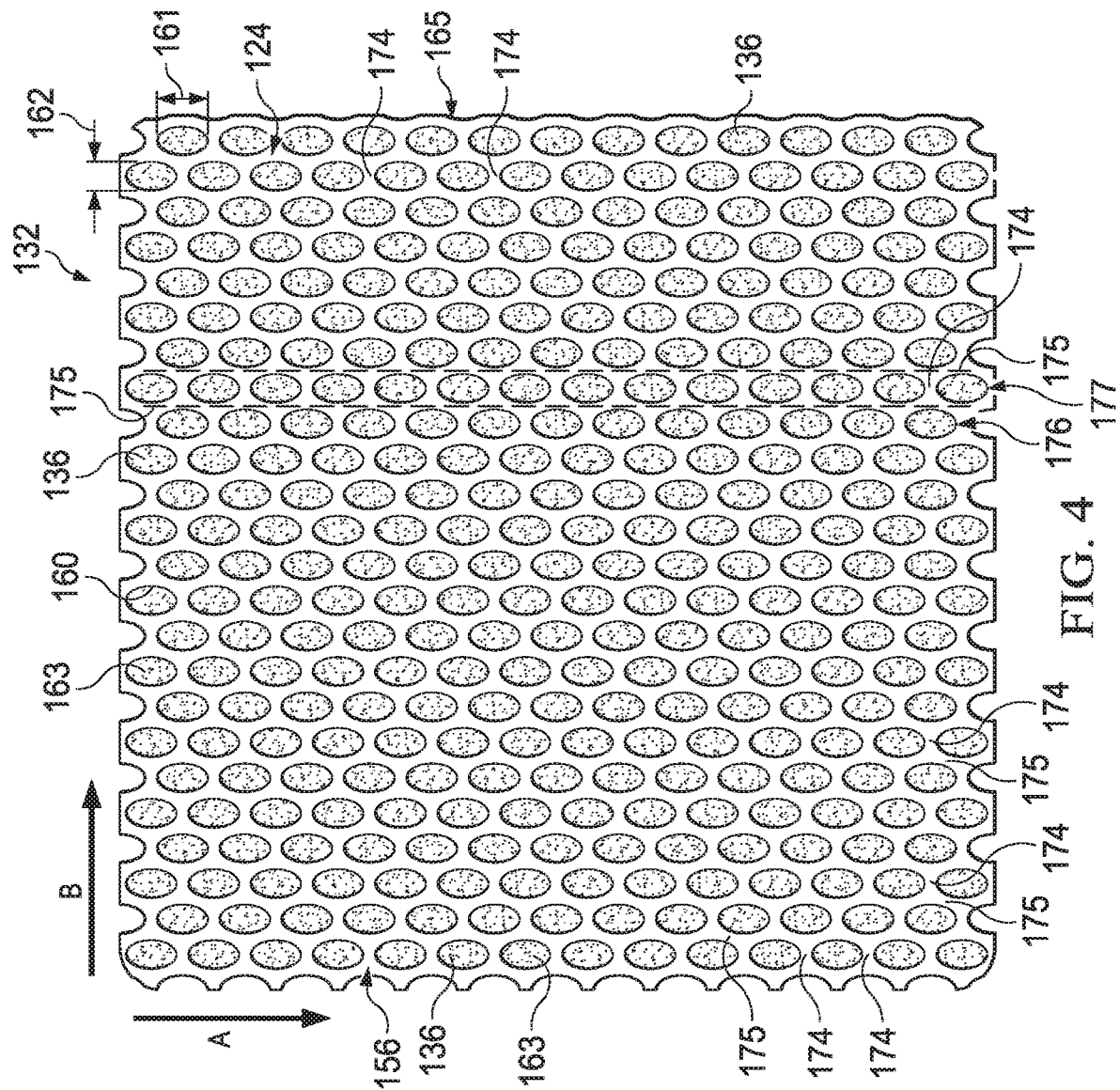
FIG. 4 is a plan view of an illustrative example of a base layer shown as a component of the example medical drape of FIG. 2.

Referring to FIGS. 4-6, the adherent surface 124 of the medical drape 114 may be configured to have a variable adherent force or strength. For example, the adherent surface 124 may have an adherent force or strength, such as an average adherent force, that is greater in one direction or axis along the adherent surface 124 than in another direction or axis along the adherent surface 124. Further, the adherent surface 124 may have a greater variability of adherent force or strength in one direction or axis along the adherent surface 124 than in another direction or axis along the adherent surface 124. Varying the adherent force or strength may provide improvements to the serviceability of the medical drape 114 that may include, for example, enhancement to the sealing capability of the medical drape 114, and reduction or elimination of patient pain and damage to tissue upon removal of the medical drape 114. For example, configuring the medical drape 114 with a variable adherent force or strength may permit the medical drape 114 to resist peeling or loss of adherence to tissue in one direction while allowing removal of the medical drape 114 in another direction with reduced force. In general, reducing the adherent force or reducing variations in the force, such as a peak-to-peak force amplitude, along a particular direction or axis of the medical drape 114 may reduce pain or potential damage to tissue upon removal of the medical drape 114 along that direction or axis.

In some embodiments, the adherent surface 124 may include a first adherent force profile 170 oriented along the first axis A of the medical drape 114 and a second adherent force profile 171 oriented along the second axis B of the medical drape 114. In some embodiments, the first axis A may be positioned substantially perpendicular to the second axis B. Further, in some embodiments, the first axis A may be coplanar to the second axis B.

The first adherent force profile 170 may have an average adherent force or strength that differs from an average adherent force or strength of the second adherent force profile 171. For example, in some embodiments, the first adherent force profile 170 may have an average adherent force less than an average adherent force of the second adherent force profile 171. In some embodiments, the average adherent force of the first adherent force profile 170 may be between about 10 percent to about 50 percent less than the average adherent force of the second adherent force profile 171. Further, in some embodiments, the first adherent force profile 170 may have a first peak-to-peak force amplitude 172 less than a second peak-to-peak force amplitude 173 of the second adherent force profile 171. In some embodiments, the first peak-to-peak force amplitude 172 may be between about 50 percent to about 300 percent less than the second peak-to-peak force amplitude 173.

As shown in FIG. 4, in some embodiments, the adherent couplings may be arranged in an overlapping pattern such that at least one of the adherent couplings 163 may overlap at least a portion of a space between the adherent couplings 163 along the first axis A. Further, in some embodiments, at least one of the adherent couplings 163 may partially or entirely overlap another of the adherent couplings 163 along the first axis A. As described above, the adherent couplings 163 may have substantially the same elongate length 161 and the width 162 as the plurality of apertures 160. Thus, the adherent couplings 163 may include the elongate length 161 and the width 162 positioned normal to the elongate length 161. In some embodiments, the elongate length 161 of the adherent couplings 163 may be greater than the width 162 of the adherent couplings 163. The elongate length 161 may be oriented along the first axis A.

Similar to the adherent couplings 163, the elongate length 161 of the plurality of apertures 160 may be oriented along the first axis A and configured to overlap a space between the plurality of apertures 160 along the first axis A. In some embodiments, the plurality of apertures 160 may be spaced apart from one another, for example, on the base layer 132 or the adherent surface 124. In some embodiments, at least one of the plurality of apertures 160 may be configured to overlap another of the plurality of apertures 160 along the first axis A, or overlap at least a portion of a space between the plurality of apertures 160 along the first axis A. In some embodiments, the plurality of apertures 160 may be free of overlap along the second axis B. Further, as described above, in some embodiments, the adhesive 136 may be carried by the plurality of apertures 160 to, for example, form the adherent couplings 163.

In some embodiments, the medical drape 114 may include at least one transition region 174 positioned on the adherent surface 124 along the first axis A. The transition region 174 may be positioned between the plurality of apertures 160 or the adherent couplings 163 along the first axis A. In some embodiments, the transition region 174 may be a space or other feature configured to separate each of apertures 160 or each of the adherent couplings 163 from one another along the first axis A. In some embodiments, at least one of the apertures 160 or the adherent couplings 163 may overlap the transition region 174 along the first axis A.

In some embodiments, the medical drape 114 may include a border region 175 positioned on the adherent surface 124. The border region 175 may be positioned between the apertures 160 or the adherent couplings 163 along the second axis B. For example, the border region 175 may separate the width 162 of one of the apertures 160 or one of the adherent couplings 163 from the width 162 of another of the apertures 160 or another of the adherent couplings 163. For example, the border region 175 may be a space or portion of the base layer 132 that is free of the apertures 160 and the adherent couplings 163, or a space on the adherent surface 124 that does not intersect the adherent couplings 163. In some embodiments, the border region 175 may be substantially continuous and extend longitudinally along the first axis A. An illustrative embodiment of the border region 175 is shown in FIG. 4 in dash line extending longitudinally along the first axis A and separating the apertures 160 and the adherent couplings 163 from one another along the second axis B.

In some embodiments, the apertures 160 or the adherent couplings 163 may be positioned at least in a first row 176 and a second row 177 along the first axis A. The apertures 160 or the adherent couplings 163 may be spaced apart from one another along the first row 176 and the second row 177. In some embodiments, at least one of the adherent couplings 163 in the first row 176 may overlap another of the adherent couplings 163 in the second row 177. Similarly, in some embodiments, at least one of the apertures 160 in the first row 176 may overlap another of the apertures 160 in the second row 177. In some embodiments, at least one of the adherent couplings 163 in the first row 176 may overlap at least a portion of a space between the adherent couplings 163 in the second row 177. Similarly, in some embodiments, at least one of the apertures 160 in the first row 176 may overlap at least a portion of a space between the apertures 160 in the second row 177. In some embodiments, the first row 176 may be separated or spaced apart from the second row 177 by the border region 175. In some embodiments, the first row 176 may be substantially parallel to the second row 177. In some embodiments, the first row 176 may be positioned alongside the second row 177. Further, in some embodiments, the first row 176 may be shifted longitudinally along the first axis A relative to the second row 177, or otherwise offset relative to the second row 177. For example, the apertures 160 or the adherent couplings 163 in the first row 176 may be offset from the apertures 160 or the adherent couplings 163 in the second row 177. Thus, in some embodiments, at least one of the adherent couplings 163 or the apertures 160 in the first row 176 may be positioned between adjacent adherent couplings 163 or apertures 160 in the second row 177.

FIGS. 5A-5B provide a detail view of a first datum line 180a and a second datum line 180b moving along the first axis A of an illustrative embodiment of the base layer 132 and the adherent surface 124 of the medical drape 114. The first datum line 180a and the second datum line 180b may each correspond to an amount of adherent force at a discrete location along the first axis A that may be plotted to form part of the first adherent force profile 170 along the first axis A. The first datum line 180a and the second datum line 180b are shown extending along the adherent surface 124 substantially perpendicular to the first axis A to illustrate removal or peeling of the medical drape 114 from tissue along the first axis A. As shown in FIG. 5A, the first datum line 180a intersects a portion of the adherent couplings 163 and a portion of the base layer 132 free of the adherent couplings 163. Similarly, the second datum line 180b in FIG. 5B intersects a portion of the adherent couplings 163 and a portion of the base layer 132 free of the adherent couplings 163. Thus, the first datum line 180a and the second datum line 180b may each include a surface area of the adherent couplings 163 and a surface area of the base layer 132 in a ratio that may be referred to as an adherent coupling to base layer ratio. Along the first axis A, at least one of the adherent couplings 163 may overlap a space, such as the transition region 174, between another of the adherent couplings 163. In such a configuration, the adherent coupling to base layer ratio may remain greater than zero or have less variation at both the first datum line 180a and the second datum line 180b because, for example, the adherent couplings 163 and the base layer 132 each contribute to the adherent force at each location along first axis A.

As described above, portions of the base layer 132 free of the adherent couplings 163 may have less adherent force than the adherent couplings 163. The adherent coupling to base layer ratio at a discrete location or datum on the adherent surface 124 may define, determine, or correspond to an adherent force at that discrete location or datum. For example, reducing the surface area of the adherent couplings 163 relative to the base layer 132, or reducing the adherent coupling to base layer ratio, may reduce the adherent force. Further, reducing variation in the adherent coupling to base layer ratio moving along an axis of the medical drape 114 may reduce variation in the adherent force profile, for example, by reducing the peak-to-peak force amplitude of the adherent force profile. Such a reduced variation in the adherent coupling to base layer ratio may provide a substantially constant or flat adherent force profile. A reduced adherent force and/or a reduced variation in adherent force along the adherent surface 124 may provide reduced pain and damage to tissue upon removal of the medical drape 114.

FIGS. 5C-5D provide a detail view of a first datum line 182a and a second datum line 182b moving along the second axis B of an illustrative embodiment of the base layer 132 and the adherent surface 124 of the medical drape 114. The first datum line 182a and the second datum line 182b may each correspond to an amount of adherent force at a discrete location along the second axis B that may be plotted to form part of the second adherent force profile 171 along the second axis B. The first datum line 182a and the second datum line 182b are shown extending along the adherent surface 124 substantially perpendicular to the second axis B to illustrate removal or peeling of the medical drape 114 along the second axis B. As shown in FIG. 5C, the first datum line 182a intersects a portion of the adherent couplings 163 and a portion of the base layer 132 free of the adherent couplings 163. In contrast, the second datum line 182b in FIG. 5D intersects only the base layer 132 without intersecting any of the adherent couplings 163. Thus, as the medical drape 114 is peeled or removed along the second axis B, the adherent coupling to base layer ratio drops to zero at the second datum line 182b, which may indicate a higher variation in adherent force along the second axis B compared to the first axis A. As shown in FIGS. 5C-5D, the border region 175 may separate the adherent couplings 163 from overlapping one another along the second axis B, which may cause the adherent coupling to base layer ratio to have greater variation along the second axis B than the first axis A.

Referring to FIG. 6, the first adherent force profile 170 provides a graphical illustration of adherent force or load plotted versus time as the medical drape 114 was removed from tissue along the first axis A during a test. Similarly, the second adherent force profile 171 provides a graphical illustration of adherent force or load plotted versus time as the medical drape 114 was removed from tissue along the second axis B during the test. The adherent force or load was measured in Newtons and plotted versus time in seconds. The test results show that the first adherent force profile 170 along the first axis A has a lower average adherent force than the average adherent force of the second adherent force profile 171 along the second axis B. Further, the test results show that the first adherent force profile 170 has a lower peak-to-peak force amplitude 172 than the peak-to-peak force amplitude 173 of the second adherent force profile 171 along the second axis A. In such a configuration, removal of the medical drape 114 along the first axis A may cause less patient pain and tissue damage than removal along the second axis B. However, the second axis B may provide a more secure connection to tissue or other components of the system than the first axis A. Therefore, a user may position the medical drape 114 at the tissue site 102 in an orientation such that an edge or portion of the medical drape 114 most at risk of peeling may be substantially aligned with the second axis B, having a greater average adherent force than the first axis A. Subsequent removal of the medical drape 114 may occur along the first axis A, having less adherent force and less variation in adherent force than the second axis B.

Figure 8:
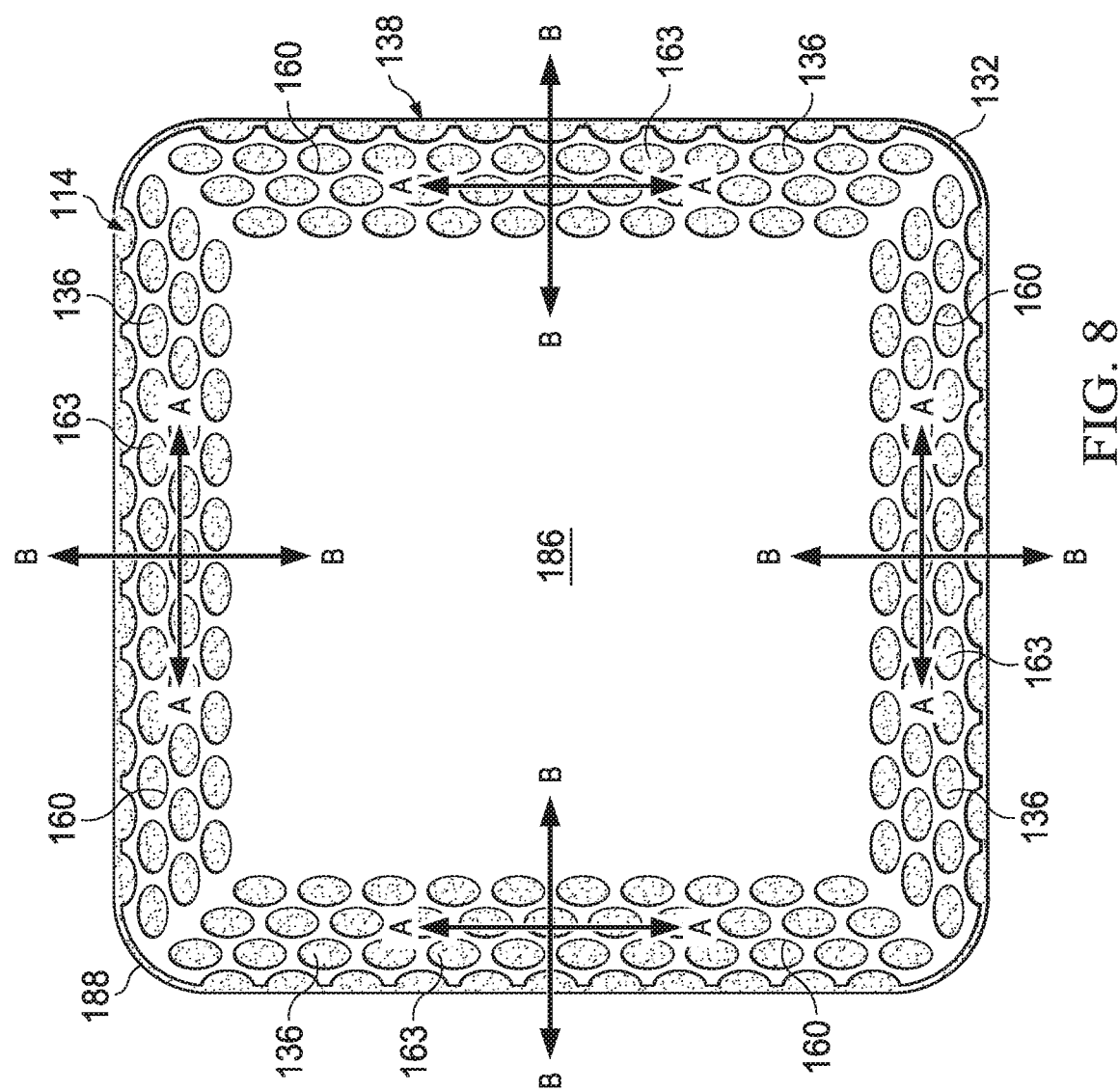
FIG. 8 is a plan view of another illustrative example of a medical drape and a cover.

Referring to FIGS. 7-8, in some embodiments, the medical drape 114 may be used or adapted for use, without limitation, to provide, to maintain, or to strengthen a seal or connection between or among components of the system 100 or portions of the tissue site 102. For example, in some embodiments, the system 100 may include an optional cover 186. The cover 186 may be adapted to be positioned on the outward-facing side 117 of the manifold 112, for example, to enhance or to provide the sealed space 118 at the tissue site 102, which may contain the manifold 112. In some embodiments, the cover 186 may be adapted to extend partially or entirely across the outward-facing side 117 of the manifold 112. The medical drape 114 may be used in combination with the cover 186 or other components of the system 100 to provide the sealed space 118.

In some embodiments, the medical drape 114 may be adapted to be positioned at, beyond, or proximate to a periphery 188 of the cover 186. The periphery 188 of the cover 186 may define an outer boundary of the cover 186. As described above, the medical drape 114 may include an average adherent force along the first axis A of the medical drape 114 that is less than an average adherent force along the second axis B of the medical drape 114. In some embodiments, the first axis A of the medical drape 114 may be oriented or positioned along the periphery 188 of the cover 186. Further, in some embodiments, the second axis B of the medical drape 114 may be adapted to be substantially aligned or positioned normal to the periphery 188 of the cover 186, which may prevent the cover 186 from peeling or losing adherence. Further, in some embodiments, the second axis B of the medical drape 114 may be adapted to be positioned substantially perpendicular to the periphery 188 of the cover 186. In such configurations, the medical drape 114 may enhance the seal provided by the cover 186 and may prevent or eliminate peeling of the cover 186 away from the tissue site 102 during use.

Referring to FIG. 7, in some embodiments, one or more of the medical drape 114 may be adapted to overlap at least a portion of the periphery 188 of the cover 186 and tissue around a periphery of the tissue site 102, such as the epidermis 106. For example, in some embodiments, the medical drape 114 may be a plurality of medical drapes 114a, 114b, 114c, and 114d that may be positioned around the periphery 188 of the cover 186 and tissue around a periphery of the tissue site 102. The medical drapes 114a, 114b, 114c, and 114d may be configured in strips as shown in FIG. 7, or another elongate shape. However, the medical drapes 114a-d may have other shapes without limitation. Further, in some embodiments, the cover 186 may be adapted to be positioned between the medical drape 114 and tissue around the periphery of the tissue site 102. Further, in some embodiments, the adherent surface 124 of the medical drape 114 may be adapted to face the cover 186 and the tissue site 102. Further, in some embodiments, the optional sealing member 138 may include a first liquid impermeable film and the cover 186 may include a second liquid impermeable film.

Other embodiments are possible. As shown in FIG. 8, a single medical drape 114 may be configured in a similar manner as the medical drapes 114a-d. For example, in some embodiments, the adherent couplings 163 may be positioned in an overlapping configuration around the periphery of the base layer 132 of the medical drape 114. Thus, the first axis A may be substantially aligned or positioned along a periphery of the base layer 132 of the medical drape 114, while the second axis B may be positioned normal to the second axis A. Further, the sealing member 138 and the cover 186 may be a unitary sheet of liquid impermeable film, or the sealing member 138 may be eliminated.

In operation according to some illustrative embodiments, the manifold 112 may be disposed proximate to the tissue site 102. The medical drape 114 may be applied over or covering the manifold 112 and the tissue site 102 to form the sealed space 118. In embodiments including the cover 186, the cover 186 may be applied over or covering the manifold 112 and the tissue site 102, and the medical drape 114 may be applied at the periphery 188 of the cover 186. In applying the medical drape 114, depending on the embodiment, the base layer 132 may be applied covering portions of the manifold 112, the tissue site 102, tissue around the tissue site 102, or the cover 186. The tackiness of the base layer 132 may initially hold or tack the medical drape 114 in position at the tissue site 102. However, if an adjustment is desired, the initial tack of the base layer 132 may be configured to permit release or removal of the medical drape 114 to facilitate such an adjustment or re-positioning. Once the medical drape 114 is in a desired position, a user may apply pressure to an exterior facing side of the medical drape 114, such as an exterior facing side of the sealing member 138, to cause at least some portion of the adhesive 136 to extend through or be forced outward from the plurality of apertures 160 to form the adherent couplings 163. The adherent couplings 163 may provide a firm, yet releasable attachment for contacting or coupling components of the system 100, portions of the tissue site 102, or tissue associated with the tissue site 102.

In some embodiments, a method for treating a tissue site, such as the tissue site 102, may include disposing the manifold 112 proximate to the tissue site 102, and covering the manifold 112 at the tissue site 102 with the cover 186. Further, the method may include providing the medical drape 114, which may include the adherent surface 124. As described above, the adherent surface 124 may include an average adherent force along the first axis A of the medical drape 114 that is less than an average adherent force along the second axis B of the medical drape 114. Further, the method may include positioning the adherent surface 124 of the medical drape 114 on tissue around the periphery 188 of the cover 186. The first axis A of the medical drape 114 may be oriented along the periphery 188 of the cover 186. Further, the method may include delivering reduced pressure to the manifold 112, or otherwise treating the tissue site 102.

In some embodiments, the method may include removing the medical drape 114 from the tissue around the periphery 188 of the cover 186 along the first axis A of the medical drape 114. In some embodiments, removing the medical drape 114 may include peeling the medical drape 114 away from the tissue around the periphery 188 of the cover 186 along the first axis A of the medical drape 114.

In some embodiments, the method may include positioning the second axis B of the medical drape 114 normal to the periphery 188 of the cover 186. In some embodiments, the method may include overlapping the periphery 188 of the cover 186 and at least a portion of the tissue around the periphery 188 of the cover 186 with the medical drape 114. In some embodiments, the method may include positioning at least a portion of the medical drape 114 on the periphery 188 of the cover 186.

In some embodiments, the medical drape 114 may include the base layer 132, the sealing member 138, and the adhesive 136 configured as described above. In such embodiments, the method may include applying a force to an exterior facing side of the sealing member 138 to cause at least a portion of the adhesive 136 to extend through the plurality of apertures 160 in the base layer 132 into contact with the tissue around the periphery 188 of the cover 186.

In some embodiments, a method for treating a tissue site, such as the tissue site 102, may include providing the medical drape 114 adhered to a tissue at the tissue site 102. The medical drape 114 may include the adherent surface 124. The adherent surface 124 may include an average adherent force along the first axis A of the medical drape 114 that is less than an average adherent force along the second axis B of the medical drape 114. Further, the method may include removing the medical drape 114 from the tissue. The step of removing the medical drape 114 may include peeling the medical drape 114 away from the tissue along the first axis A of the medical drape 114.

Although the subject matter of this disclosure has been provided by way of example in the context of certain illustrative, non-limiting embodiments, various changes, substitutions, permutations, and alterations can be made without departing from the scope of this disclosure as defined by the appended claims. Any feature described in connection to any one embodiment may also be applicable to any other embodiment. As such, the benefits and advantages described above may relate to one embodiment or may relate to several embodiments. Further, the steps of the methods described herein may be carried out in any suitable order, or simultaneously where appropriate.

What is claimed is:

1. A medical drape for treating a tissue site, comprising:
an adhesive pattern on an adherent surface including first adherent force profile oriented along a first axis and a second adherent force profile oriented along a second axis, the first adherent force profile having an average adhesive force less than an average adhesive force of the second adherent force profile; and
a plurality of adherent couplings positioned on the adherent surface to define the adhesive pattern, the plurality of adherent couplings positioned at least in a first row and a second row along the first axis, at least one of the plurality of adherent couplings in the first row overlapping at least a portion of a space between the plurality of adherent couplings in the second row, wherein the first row is separated from the second row by a border region extending linearly along the first axis.

2. The medical drape of claim 1, wherein the adherent couplings have an aspect ratio between about 1.2 to about 1.8.

3. The medical drape of claim 1, wherein the adherent couplings have an elongate shape.

4. The medical drape of claim 1, wherein the first axis is positioned substantially perpendicular to the second axis.

5. The medical drape of claim 1, wherein the first adherent force profile has a peak-to-peak force amplitude less than a peak-to-peak force amplitude of the second adherent force profile.

6. The medical drape of claim 1, wherein at least one of the plurality of adherent couplings overlaps at least a portion of another of the adherent couplings along the first axis.

7. The medical drape of claim 1, further comprising at least one transition region positioned on the adherent surface and between the plurality of adherent couplings along the first axis.

8. The medical drape of claim 7, wherein at least one of the plurality of adherent couplings overlaps the transition region along the first axis.

9. The medical drape of claim 1, wherein the plurality of adherent couplings are spaced apart from one another on the adherent surface such that at least a portion of the adherent surface is free of the plurality of adherent couplings, and wherein the plurality of adherent couplings have a greater adherent force than the portion of the adherent surface free of the adherent couplings.

10. The medical drape of claim 1, wherein the plurality of adherent couplings comprise an elongate length and a width positioned normal to the elongate length, and wherein the elongate length is greater than the width and oriented along the first axis.

11. The medical drape of claim 1, wherein the plurality of adherent couplings are spaced apart from one another along the first row and the second row.

12. The medical drape of claim 1, wherein at least one of the adherent couplings in the first row is positioned between adjacent couplings in the second row.

13. The medical drape of claim 1, further comprising:
a base layer comprising a first side, a second side opposite the first side, and a plurality of apertures disposed through the base layer between the first side and the second side, the first side carrying the adherent surface;
an adhesive positioned on the second side of the base layer and adapted to extend through the plurality of apertures to the first side to form the plurality of adherent couplings on the adherent surface.

14. The medical drape of claim 13, further comprising a sealing member adapted to cover the second side of the base layer, wherein the adhesive is positioned between the sealing member and the base layer and adapted to extend through the plurality of apertures when a force is applied to an exterior surface of sealing member.

15. The medical drape of claim 14, wherein the sealing member comprises a liquid impermeable film.

16. The medical drape of claim 13, wherein the base layer comprises at least one of the following: silicone, hydrocolloid, hydrogel, polyurethane gel, and polyolefin gel.

17. The medical drape of claim 13, wherein the adhesive comprises at least one of the following: an acrylic adhesive and a tacky silicone adhesive.

18. A system for treating a tissue site comprising the medical drape of claim 1, wherein the medical drape is adapted to provide a sealed space relative to the tissue site, the system further comprising:
   a manifold adapted to be disposed in the sealed space and to distribute reduced pressure to the tissue site; and
   a reduced-pressure source for fluidly coupling to the sealed space.

* * * * *